United States Patent [19]

Lee et al.

[11] 4,426,306

[45] Jan. 17, 1984

[54] ANTIOXIDANTS AND LUBRICATING OIL CONTAINING SAME

[75] Inventors: Richard J. Lee, Downers Grove, Ill.; Lynn M. R. Murphy, Lafayette, La.

[73] Assignee: Standard Oil Company (Indiana), Chicago, Ill.

[21] Appl. No.: 420,304

[22] Filed: Sep. 20, 1982

Related U.S. Application Data

[62] Division of Ser. No. 59,246, Jul. 20, 1979, Pat. No. 4,390,437.

[51] Int. Cl.$^3$ ............................ C10M 1/20; C10M 1/32
[52] U.S. Cl. ........................... 252/51.5 A; 252/51.5 R; 252/403; 544/363; 544/365; 546/168; 546/169; 546/314; 546/323
[58] Field of Search ............... 252/51.5 A, 51.5 R, 252/403; 544/363, 365; 546/168, 169, 314, 323

[56] References Cited

U.S. PATENT DOCUMENTS

2,198,961  4/1940  Dietrich ...................... 252/51.5 R
3,585,141  6/1971  Ingersoll ...................... 252/62.51

FOREIGN PATENT DOCUMENTS

829494  3/1960  United Kingdom .......... 252/51.5 R

*Primary Examiner*—W. J. Shine
*Attorney, Agent, or Firm*—Dragan J. Karadzic; William T. McClain; William H. Magidson

[57] ABSTRACT

This invention relates to improved hydrocarbon lubricating oil compositions. More particularly this invention relates to hydrocarbon oil compositions which possess improved oxidation inhibition properties through the presence of a new additive functioning as an antioxidant or as an antioxidant catalyst which acts as a chain terminating species for oxidation reactions.

6 Claims, No Drawings

ANTIOXIDANTS AND LUBRICATING OIL CONTAINING SAME

This is a division of application Ser. No. 059,246 filed July 20, 1979 now U.S. Pat. No. 4,390,437.

It is known that under conditions of use lubricating oils come into contact with oxygen at elevated temperatures in the presence of metals or other compounds that promote oxidation with the result that the lubricant undergoes a series of oxidation reactions causing an increase in the viscosity of the lubricant, the formation of carbonaceous matter, and the development of acidic contaminants within the oil which can be corrosive to engine components. The oxidation of lubricating oils involves a chain reaction in which organic peroxides attack unoxidized oil and are subsequently regenerated by oxygen in the air to continue such attack. An antioxidant system can prevent oxidation of oils if it is capable of performing two inhibition functions comprising the destruction of peroxy radicals thereby causing the chain oxidation reaction to cease, and the conversion of any hydroperoxides (formed in preventing the undesirable reactions of the peroxy radicals) into nonradical products before the hydroperoxides can thermally decompose into new free radicals to further propagate the chain oxidation reaction. Alkyl disulfides are widely used as additives to generate non-radical species from hydroperoxides, but the hydroperoxide disulfide reaction often can be slower than the rapid thermal decomposition of hydroperoxide. Therefore, a compound that can function as a chain terminating species would act as a catalyst to increase the rate of non-radical producing reactions relative to the rate of the radical producing reactions. Such a compound would function as an antioxidation catalyst and have increased efficiency as an antioxidant. Several of the typical additives commonly incorporated into hydrocarbon oils are effective oxidation inhibitors but don't function as antioxidation catalysts and can be expensive to produce. Others are inefficient in that they do not counteract all the effects of oxidation. A continuing need exists for improved lubricant compositions containing antioxidants efficient under conditions of use that can be economically produced.

It is the object of this invention to provide lubricant compositions which are resistant to oxidative deterioration. Another object is to provide lubricant compositions containing compounds effective as oxidation inhibitors. A further object is to provide lubricant compositions containing compounds which act as catalysts to increase the rate of non-radical producing reactions relative to the rate of radical producing reactions. A further object is to provide a method to predict which antioxidant compounds will function as such catalysts. Other objects appear hereinafter.

We have found that these objects can be attained by producing new lubricant compositions comprising a major amount of a hydrocarbon oil and a small percentage of an oil soluble compound containing an antioxidant functional group selected from the following: pyridyl phenyl ketimine, pyridyl 2,6-dialkyl 1-hydroxy phenyl ketimine, nicotinyl, 8-carbonyl quinoline, and dipyridyl. It is possible to determine which of these compounds can act as antioxidation catalysts by relating viscosity changes with time of the individual lubricant composition containing each to the energy required to form the radical ion of the corresponding compound or to the polarographic half-wave potential of the corresponding compound. Thus while all of the lubricant compositions of the present invention contain effective new antioxidants, those compositions containing a compound that can function as an antioxidation catalyst are superior in efficiency.

The lubricant compositions of the present invention comprise a major amount of a hydrocarbon oil and from about 0.1% to 10% of an additive with the structure $A[(X)_{m-1}Y]_n$ wherein A comprises an antioxidant functional group, $[(X)_{m-1}Y]$ comprises an oil soluble moiety connected directly to A, and n is a whole number from 1 to 2 and corresponds to the number of free valences in A. The antioxidant functional group is selected from the following five classes of structures:

(1) pyridyl phenyl ketimine

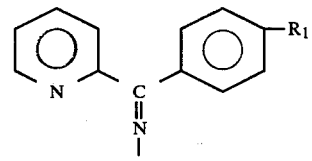

wherein $R_1$ is hydrogen, alkyl, alkenyl, or aryl, (2) pyridyl 2,6-dialkyl 1-hydroxy phenyl ketimine

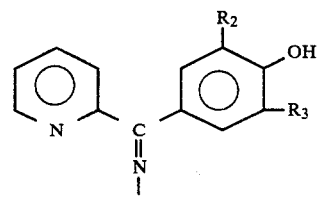

wherein $R_2$ and $R_3$ are alkyl groups (3) nicotinyl

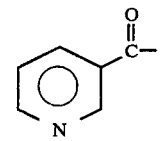

(4) 8-carbonyl quinoline

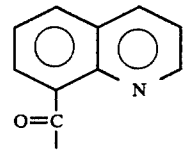

(5) dipyridyl

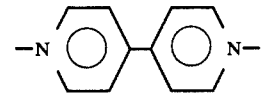

Oil solubility is provided to the above functional group by $[(X)_{m-1}Y]$ wherein X, which is connected directly to A and Y, is selected from the group consisting of succinyl, imine, amino, and dialkyl piperazine succinimide having the structures:

$$-\overset{O}{\underset{\|}{C}}-CH_2-CH_2-\overset{O}{\underset{\|}{C}}- \quad (i)$$

$$-\underset{H}{\overset{|}{C}}=N- \quad (ii)$$

$$-\underset{|}{\overset{H}{N}}- \quad (iii)$$

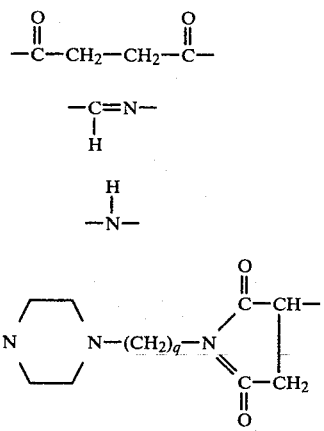

(iv)

wherein p and q are whole numbers from 1 to 6. Y is a monovalent aliphatic chain of from 12 to 50 carbon atoms and m is a whole number from 1 to 2. Y's valence is connected directly to X when m is 2 and directly to A when m is 1. When X is succinyl or imine and m is 2, A can only be dipyridyl and n is 2. When X is amino or dialkyl piperazine succinimide and m is 2, A can be any of the five previously designated structures and n is 1 or 2 as appropriate. When m is 1, A can be any of the five previously designated structures and n is 1 or 2 as appropriate.

Suitable aliphatic chains comprising Y include alkyls, alkenyls, and polymers of $C_2$ or higher olefins. Examples include hydrocarbyl chains of at least 12 carbon atoms, such as a $C_{12}$ to $C_{50}$ straight chained or branched alkyl group like dodecyl, tridecyl, tetradecyl, hexadecyl, octadecyl, etc. or alkenyl group such as dodecenyl, tridecenyl, tetradecenyl, hexadecenyl, octadecenyl, dodecadienyl, tridecadienyl, tetradecadienyl, hexadecatrienyl, octadecatrienyl, etc. Also suitable are $C_{12}$ to $C_{50}$ polymers of $C_2$ or higher olefins such as polyethylene, polypropylene, polybutylene, and similar compounds. These polymers are usually generated from refinery streams by polymerization in the presence of a suitable catalyst such as aluminum chloride. When X is a dialkyl piperazine succinimide and Y is an olefin polymer, olefin polymers of about twelve to thirty-five carbons are preferred. When X is amino, a primary amino group with Y as a straight chained $C_6$ to $C_{20}$ alkyl, alkenyl, or polymer is preferred. A single primary amino group is employed to avoid crosslinking reactions. Except when A is dipyridyl, it is preferred that the moiety providing oil solubility to the additive not be attached directly to the pyridine group in the part A antioxidant moiety, but rather be attached directly to the molecule at the free valence position previously indicated in each part A structure.

The hydrocarbon component can be any synthetic or natural hydrocarbon oil such as petroleum oil, preferably with a viscosity about 40 to 110 Saybolt Universal Seconds at 100° C. The present invention is particularly adapted to oils for use in automobile and other types of spark ignition engines. Therefore, fully formulated oils that pass the current MS Test Sequences are preferred.

It is possible to determine which of these antioxidant additives can function as chain terminating species and therefore catalytically increase the rate of non-radical producing reactions relative to the rate of radical producing reactions by relating viscosity changes with time of the individual lubricant composition containing each to the polarographic half-wave potential of the corresponding additive or to the energy required to form the radical ion of the additive in the following way. The ground state of a molecule is that of the most stable distribution of electrons. The formation of a radical ion is a single electron transfer process and the radical ion occupies the nearest unoccupied molecular orbital to the ground state. If the energy required to enter the nearest unoccupied molecular orbital is too low, a radical ion will not be formed but rather an excited molecule results. These molecules can be effective antioxidants but don't function as chain terminating species. If the energy required to enter the nearest unoccupied molecular orbital is sufficient to form a radical ion the compound can function as an antioxidant catalyst since the radical ion comprises a chain terminating species in the oxidation chain reaction. These compounds therefore can increase the rate of non-radical producing reactions and thereby catalyze antioxidation reactions.

The energy required to enter the nearest unoccupied molecular orbital is linearly related to half-wave potentials determinable by polarography for specific compounds. Also the energy of the nearest unoccupied molecular orbital calculated in accordance with Huckel Molecular Orbital Theory is linearly related to polarographic half-wave potentials. See Streitwiser, Jr., A., "Molecular Orbital Theory for Organic Chemists," John Wiley & Sons, Inc., New York, 1961. HMO parameters have been developed by W. Paudler and T. Kress to generate a linear correlation of polarographic half-wave potentials with the calculated energy of the nearest unoccupied molecular orbital for various nitrogen heterocyclic aromatic compounds. See Castle, R., Ed., "Topics in Heterocyclic Chemistry" Wiley-Interscience, New York, pp. 86–121, 1969. We have found using the Paudler & Kress energy data that the calculated energy required to form the radical ion of a compound is linearly related to inhibited air oxidation rates of a lubricant composition containing that compound expressed by viscosity changes in the lubricant over an extended period of time. Thus the viscosity changes of a lubricant with time can be related to the polarographic half-wave potential and the energy required to form the radical ion of the additive used in that lubricant.

Using this relationship we have found that antioxidant additives with calculated energies of the nearest unoccupied molecular orbital greater than or equal to 0.7 whose corresponding lubricant viscosities require greater than or equal to 60 of use to increase to four times the initial viscosity or whose corresponding polarographic half-wave potential is about 1.3 or more volts function as antioxidant catalysts. Thus by considering calculated energies of the nearest unoccupied molecular orbital or half-wave potentials and making viscosity tests, a prediction can be made whether a specific compound will function as an antioxidation catalyst. In testing the antioxidant additives of the present invention, it was established that the compounds of the first class containing a pyridyl phenyl ketimine group were chain terminating species due to their superior performance as antioxidants. More particularly it was established that additives wherein part A is a pyridyl phenyl ketimine, X is a dialkyl piperazine succinimide, Y is a $C_{12}$ to $C_{50}$ polymer, m is 2, and n is 1 functioned as chain terminating species.

Compounds containing the pyridyl phenyl ketimine group can be produced by first reacting benzoyl chloride with pyridine and then reacting the resultant product with a compound to provide oil solubility. Oil solubility can be provided by any of several different moieties as previously described. Preferred for reaction with the antioxidant of the first class is a moiety wherein X is a dialkyl piperazine succinimide and Y is an olefin polymer.

Solvents appropriate for the production of pyridyl phenyl ketimine compounds include nonreactive hydrocarbons with a minimum boiling temperature of 100° C. Examples include alkanes such as octane, nonane, decane or aromatics such as toluene, xylene, ethylbenzene, propylbenzene, cumene, butylbenzene, toluidine, and others. Preferred is an aromatic solvent such as xylene.

In somewhat greater detail the pyridyl phenyl ketimine antioxidants are generated by reacting benzoyl chloride and pyridine and subsequently reacting the product with a compound to provide oil solubility in an appropriate solvent. The reaction can be carried out at atmospheric pressure at temperatures from 100° C. to 300° C., preferably at the refluxing temperature of the reaction mixture. After completion of the reaction the solvent can be separated by distillation of the reaction mixture and byproducts precipitated and removed by filtration. The reaction solution can then be stripped by vacuum under reduced pressure to generate the desired pyridyl phenyl ketimine compound.

To effect the reaction for generating these ketimine antioxidants benzoyl chloride is introduced into a conventional glass reactor containing pyridine in molar excess of up to 20:1 of pyridine to benzoyl chloride. Heat is applied to the system to obtain a temperature of about 120° C. to initiate refluxing of the reaction mixture. The compound chosen to provide oil solubility is then added and the reaction mixture is again heated to reflux. Preferably a molar ratio of 1:1 of benzoyl chloride to oil soluble compound is utilized.

The reaction can be carried out at temperatures of 100° C. to 300° C. The refluxing temperature of the reaction mixture is preferred since it provides a means of easily controlling the reaction. Use of a lower temperature results in little if any reaction. At the refluxing temperature the reaction can be conducted at atmospheric pressure.

After completion of the reaction the solvent can be separated by distillation. The reaction mixture can then be treated with a basic compound such as barium hydroxide to precipitate chlorides, which can be removed by filtration or other appropriate means of separating solids and liquids. The resulting solution can be stripped on vacuum under reduced pressure to generate the desired pyridyl phenyl ketimine antioxidant. The pressure used varies with the temperature employed which should not exceed 120° C.

Spot dispersancy and viscosity tests have shown that the pyridyl phenyl ketimine compound generated is useful as an effective antioxidant in lubricants. Additionally it is also effective as a chain terminating species and therefore functions as an antioxidation reaction catalyst. The remaining four classes of antioxidant compounds have been found to be effective antioxidants although they do not function as antioxidation catalysts.

The second class of antioxidant compounds which contain a pyridyl 2,6-disubstituted 1-hydroxy phenyl ketimine group can be produced by first reacting nicotinic acid with an acid chloride in a pyridine solvent, and then subsequently reacting the nicotinic acid chloride obtained with a hindered phenol in the presence of a Lewis acid catalyst. After removal of the catalyst an oil soluble moiety is then added onto the compound. The desired antioxidant can then be separated from the reaction mixture by distillation.

Typical acid chlorides such as thionyl chloride, phosphorus trichloride, and phosphorus pentachloride are used to convert the nicotinic acid into its acid chloride derivative prior to addition of the hindered phenol. Thionyl chloride is preferred for convenience since any excess is easily separated from the reaction mixture and any byproducts formed are gases.

Suitable phenols include those with two substituents each of which is ortho to the hydroxy group. The substituents are normally alkyl groups such as methyl, ethyl, propyl, butyl, etc. Phenols with tertiary-butyl groups ortho to the hydroxy group are preferred for use in preparing the pyridyl substituted phenyl ketimine antioxidant compound. Lewis acid catalysts appropriate for use in the reaction include typical compounds such as aluminum chloride, boron trifluoride, stannic chloride, or zinc chloride. Aluminum chloride is preferred in the reaction.

After formation of the antioxidant functional group a compound to provide oil solubility to the antioxidant is added. Suitable compounds are as previously discussed. Preferred is a moiety wherein X is amino and Y is a $C_{12}$ to $C_{20}$ alkyl such as N-octadecyl amine.

To effect the reaction an acid chloride, preferably thionyl chloride, is added to an excess amount of pyridine containing nicotinic acid in a conventional reactor. A mole ratio of 1:1 to 5:1 of thionyl chloride to nicotinic acid can be used with 2:1 being the preferred ratio. The reaction mixture is heated to about 135° C. to initiate refluxing. After formation of the acid chloride derivative of nicotinic acid, the hindered phenol and Lewis acid catalyst, preferably aluminum chloride, are then added with stirring for several hours at ambient temperature. A mole ratio of 1:1 of phenol to nicotinic acid chloride is preferred but ratios of 0.5:1 to 1:1 can be used.

The entire reaction mixture is then dissolved in an aromatic solvent such as toluene and washed with water to remove the aluminum chloride catalyst. The compound chosen to provide oil solubility is added to the toluene mixture and refluxed at about 135° C. A mole ratio of 1:1 of nicotinic acid to oil soluble compound is preferred but a mole ratio up to 1:2 can be used. After completion of the reaction toluene and water can be separated by azeotropic distillation. The desired product can be identified by infrared spectroscopy. The pyridyl 2,6-dialkyl 1-hydroxy phenyl ketimine compound acts as an effective antioxidant in lubricating oil compositions.

The compounds of the third class of antioxidants containing a nicotinyl functional group can be prepared by first forming the acid chloride derivative of nicotinic acid and subsequently substituting the desired group providing oil solubility.

The preparation can be carried out by first reacting nicotinic acid in a pyridine solvent with an appropriate chloride compound such as thionyl chloride, sulfuryl chloride or phosphorus trichloride. A mole ratio of 2:1 chloride to acid is preferred but ratios from 1:1 to 5:1 can be used. To the resulting reaction mixture is added an oil soluble entity in an appropriate solvent in the presence of a Lewis acid catalyst. The preferred oil soluble entity for use with antioxidants of the third class is one wherein X is amino and Y is a $C_{12}$-$C_{20}$ alkyl. A mole ratio range of 1:1 to 1:2 acid to oil soluble compound can be used with 1:1 being preferred. Suitable solvents for the oil soluble compound include nonpolar aromatic hydrocarbons such as benzene, toluene, xylene, ethylbenzene, propylbenzene and similar compounds. Suitable Lewis acid catalysts include aluminum choride, boron trifluoride, stannic chloride, and zinc chloride. Aluminum chloride is preferred.

The initial reaction to form the acid chloride can be carried out at the refluxing temperature of the reaction mixture which when using pyridine is about 135° C. After the oil soluble compound and catalyst are added to the reaction mixture the addition of heat is no longer necessary since the reaction will proceed at room temperature with stirring. Both reactions proceed at atmospheric pressure.

The desired nicotinyl antioxidant additive can be separated from the reaction mixture by washing the reaction mixture with water and stripping under vacuum. The water wash separates the catalyst from the reaction mixture. The solvent is separated by stripping under vacuum to yield the desired product. The nicotinyl compound obtained is an effective antioxidant in lubricant compositions.

The fourth class of compounds containing an 8-carbonyl quinoline group can be prepared by reacting quinoline with an acid chloride derivative of a long chain carboxylic acid in an appropriate solvent in the presence of a Lewis acid catalyst.

Suitable acid chlorides include those derived from carboxylic acids with at least 12 carbon atoms such as lauryl chloride, myristyl chloride, palmitoyl chloride, stearoyl chloride, oleyl chloride, and the like. Preparation of such acid chlorides from the corresponding carboxylic acids is well known. Solvents appropriate for the reaction include nonpolar chlorinated solvents such as dichloromethane, carbon tetrachloride, or chloroform. Dichloromethane is preferred to the others. A Lewis acid is used to catalyze the preparation of the carbonyl quinoline compounds. Typical Lewis acids such as aluminum chloride, boron trifluoride, stannic chloride, or zinc chloride can be used, but aluminum chloride is preferred.

In somewhat greater detail the carbonyl quinoline antioxidants can be generated by reacting quinoline with an acid chloride such as palmitoyl chloride in a nonpolar chlorinated solvent such as dichloromethane in the presence of an aluminum chloride catalyst. The reaction can be carried out at the refluxing temperature of the solvent at atmospheric pressure. The reaction can be terminated by the addition of water which is then removed and the desired product can be isolated by separating solids by filtration and stripping the solvent under vacuum.

To initiate the reaction for preparing the carbonyl quinoline compound an acid chloride such as palmitoyl chloride is dissolved in solvent, preferably dichloromethane, in a conventional glass reactor. Nitrogen gas is introduced into the system to eliminate air and the aluminum chloride catalyst and quinoline are then added. A mole ratio of 1:1 to 1:2 of quinoline to acid chloride can be used with 1:1 preferred. Heat is then added to the system to initiate the reaction.

The reaction can be carried out at a temperature of 35° C. to 135° C. and is preferably carried out at the refluxing temperature of the solvent employed. This is approximately 40° C. when dichloromethane is used. Use of the refluxing temperature provides easy control of the reaction at atmospheric pressure.

The reaction can be terminated by the addition of water which will then effect a phase separation upon standing. The catalyst can be removed with the water layer. The final product can then be isolated from solvent and impurities by purging the remaining solution with nitrogen gas, filtering, and stripping under vacuum. The carbonyl quinoline compound generated has been shown by spot dispersancy and viscosity tests to be an effective antioxidant in lubricant compositions.

The dipyridyl compounds of the fifth class can be prepared by reacting pyridine with an oil soluble compound in the presence of zinc.

Suitable oil soluble compounds include those previously discussed with regard to all classes of claimed antioxidants. Especially appropriate for use in preparation of the dipyridyl compounds of the fifth class is a moiety wherein X is succinyl and Y is a $C_{12}$-$C_{50}$ olefin polymer. A polymer substituted succinic anhydride may be employed. Use of an anhydride requires the use of an acid chloride to convert the anhydride into an acyl chloride prior to reaction with pyridine. Suitable acid chlorides include thionyl chloride, sulfuryl chloride, phosphorus oxytrichloride, etc. Thionyl chloride is preferred.

To initiate the reaction for preparing the dipyridyl antioxidant the polymer substituted succinic anhydride is added to pyridine contained in a conventional reactor. It is preferred to use an excess of pyridine so that it can act both as solvent and reactant. Heat is then applied to the system and zinc dust is added in a molar excess to initiate the formation of dipyridyl. The acid chloride is then added to the reaction mixture to generate an acyl chloride from the anhydride which can then react to become attached to the dipyridyl. A molar ratio of succinic anhydride to acid chloride of 1:1 to 2:1 can be employed with 1:1 being preferred.

The reaction can be carried out at temperatures of 95° C. to 120° C. either under pressure or under suitable reflux conditions at atmospheric pressure. Lower temperatures result in a reduced reaction rate and long reaction time rendering it preferable to maintain at least minimum refluxing conditions.

At the completion of the reaction excess zinc salts can be removed by filtration and the reaction mixture can be stripped of pyridine by vacuum distillation. Residual chlorides can be removed by a further precipitation treatment such as by the addition of a metallic hydroxide compound followed by filtration. The product generated can be identified by infrared spectroscopy. Spot dispersancy and viscosity tests conducted on the dipyridyl compound have shown it to be an effective antioxidant.

EXAMPLE 1

Two tenths of a mole of benzoyl chloride was added dropwise to 300 ml (approximately 4 moles) of pyridine in a conventional glass reactor equipped with stirring apparatus and condenser. After reacting at 120° C. for four hours, a 51% active polybutyl succinimide of bis-aminopropylpiperazine (0.2 mole polybutyl succinimide to 0.2 mole bis-aminopropylpiperazine) dissolved in xylene was added. The reaction mixture was heated to reflux at 150° C. After completion of the reaction the xylene solvent was removed by distillation, and the reaction mixture was then treated with 0.1 mole of barium hydroxide to precipitate out chlorides. The solution was filtered and stripped on vacuum at reduced pressure at 120° C. to generate the desired pyridyl phenyl ketimine compound. Identification was made by infrared spectroscopy.

This example illustrates the production of the pyridyl phenyl ketimine of NN'-diaminopropylpiperazine polybutyl succinimide which acts as a superior antioxidant by catalytically increasing the rate of nonradical producing reactions during hydrocarbon oil oxidation.

EXAMPLE 2

This example illustrates the production of octadecyl pyridyl 2,6-ditertiary butyl 1-hydroxy phenyl ketimine which is effective as an antioxidant in lubricant compositions.

One half mole (61.5 g) of nicotinic acid was dissolved in 300 ml (approximately 4 moles) of pyridine in a conventional reactor equipped with stirring apparatus and condenser. One mole of thionyl chloride was added dropwise over a 30 minute period resulting in a temperature rise of 15° C. The reaction mixture was then heated and refluxed at 135° C. for two and one half hours. After cooling 6 g of aluminum chloride were added as a catalyst and the mixture stirred until homogeneous. One half mole (103.2 g) of 2,6-di(tertiary butyl) phenol was added. A 15° C. rise in temperature resulted and the mixture was stirred at ambient temperature for 15 hours. The reaction mixture was then dissolved in an excess of toluene and washed with water to remove the aluminum chloride. One half mole (134.7 g) of N-octadecyl amine was added to the washed toluene mixture and the reaction mixture was refluxed at 135° C. for one hour. Water and toluene were then separated from the desired product by azeotropic distillation. The remaining product was then identified by infrared spectroscopy as octadecyl pyridyl 2,6-ditertiary butyl 1-hydroxy phenyl ketimine.

EXAMPLE 3

This example illustrates the production of nicotinyl octadecylamide effective as an antioxidant in lubricant compositions.

One half mole (61.5 g) of nicotinic acid was dissolved in 300 ml of pyridine contained in a conventional reactor equipped with a condenser and stirring device. The reaction mixture was heated to reflux at about 135° C. and maintained for 2½ hours. One half mole of octadecylamine dissolved in 300 ml of toluene was then added and water was removed by azeotropic distillation. Six grams of aluminum chloride and an additional 300 ml of toluene were added and the reaction mixture was stirred for 18 hours at room temperature. After completion of the reaction the mixture was washed with water to remove aluminum chloride and stripped to remove toluene to isolate the desired product. The nicotinyl octadecylamine was identified by infrared spectroscopy.

EXAMPLE 4

This example illustrates the production of the lubricant antioxidant 8-palmitoyl quinoline.

One hundred sixty five milliliters (0.55 mole) of palmitoyl chloride were dissolved in one liter of dichloromethane in a conventional reactor. Nitrogen gas was then introduced to exclude oxygen and 20 g of anhydrous aluminum chloride were added as a catalyst. Over a 30 minute period one half mole (61.5 g) of quinoline was added dropwise. The reaction mixture was then heated and refluxed under nitrogen at about 40° C. for 2 hours. After cooling the reaction mixture 100 ml of dimethylformamide were added and the reaction was permitted to continue for 30 minutes. The reaction was terminated by the addition of 500 ml of water. After phase separation upon standing the water layer containing the aluminum chloride catalyst was removed. Anhydrous calcium sulfate was added to absorb any residual water from the reaction mixture. The calcium sulfate was removed by filtration and washed with 250 ml of dichloromethane. The final product was then isolated by purging the filtrate with nitrogen gas, filtering, and stripping by vacuum to remove dichloromethane and impurities. The product was identified by infrared spectroscopy as 8-palmitoyl quinoline. It was found to contain 0.325% cobalt as an impurity from the coloring used on the calcium sulfate.

EXAMPLE 5

This example illustrates the production of NN' dipolybutyl succinyl gamma gamma' dipyridyl which is effective as an antioxidant in lubricant compositions.

A catalyst prepared by dissolving 10 g of zinc chloride in 743 ml of pyridine was added to a conventional reactor containing one half mole (300 g) of polybutylsuccinic anhydride. The reaction mixture was heated to 95° C. and 150 g of zinc dust were added. The reaction mixture was then refluxed for 24 hours at about 95° C. Fifty grams of zinc dust were then added and the mixture was reacted at about 115° C. for 18 hours. Forty milliliters (approximately 0.5 mole) of thionyl chloride were added and the reaction mixture heated for 2 hours at 105° C. After completion of the reaction, the reaction mixture was filtered to remove zinc salts and pyridine was stripped by vacuum distillation. To aid in precipitation of additional solids 300 ml of toluene were added, the solution filtered and toluene evaporated. These washings were repeated with 250 ml of hexane and 250 ml of toluene to remove chlorine containing solids, each followed by filtration and evaporation of the solvent. Residual chlorine present was precipitated by the addition of calcium hydroxide and removed by filtration. The final product was identified by infrared analysis as NN' di-polybutyl succinyl gamma gamma' dipyridyl.

EXAMPLE 6

This example illustrates the antioxidant properties of the additives generated in Examples 1 to 5 through viscosity and spot dispersancy tests on oil compositions containing each compound. Data is summarized in Table I.

Oil thickening caused by oxidation was evaluated using viscosity tests correlated with the Oldsmobile IIIC MS Sequence Test in that oils requiring thirty or more hours to increase in viscosity by 400% meet the standard of this sequence test. Control and test compositions were fully formulated oils except that the control contained no oxidation inhibitors and the test compositions each contained 1.0% to 2.5% of one of the additives generated in Examples 1–5. Each composition contained 5% drain oil from a Ford VC MS Sequence Test to catalyze oxidation. Two separate 100 gram samples of each composition were independently oxidized at approximately 175° C. in an open oxidation tube by blowing with air at a rate of 60 cubic centimeters per minute. Aliquots of each sample were taken periodically and the viscosity of each determined using a flow rate method to correlate viscosity and time. The time required for the viscosity of each composition to increase by 400% is shown in Table I.

Spot dispersancy tests conducted to measure the ability of each additive to disperse sludge and varnish correlate with the Ford VC MS Sequence Test. A spot dispersancy test rating of approximately 80% indicates an excellent dispersant under the Ford VC test standard when the additive is present at a level of 2% in sludged oil. Control and test compositions were those used in the viscosity tests. After completion of the viscosity tests, samples of each composition were heated 16 to 20 hours in a closed container at approximately 150° C. Three to ten drops of each sample were dropped onto standard white blotter paper, the specific quantity remaining constant for each test series. The diameters of the sludge and oil spots were measured after 24 hours with the difference in diameters expressed as a percentage being proportional to the ability of the blended oil to keep sludge in suspension. As shown by the data in Table I, acceptable spot dispersancy ratings were obtained for all oils showing the additives generate no adverse effects on oil dispersancy properties.

TABLE I

| Additive Functional Group | Hours to Increase Initial Viscosity Four Times | Spot Dispersancy Test, % |
| --- | --- | --- |
| Control | 24 | 77 |
| Pyridyl phenyl ketimine | 52 | 90 |
| Pyridyl 2,6-dialkyl 1-hydroxy phenyl ketimine | 47 | 89 |
| Nicotinyl | 48 | 90 |
| 8-Carbonyl quinoline | 42 | 79 |
| Dipyridyl | 46 | 73 |

EXAMPLE 7

This example illustrates that pyridyl ketimine of NN' diaminopropylpiperazine polybutyl succinimide functions as an antioxidant catalyst.

Control and test oil compositions of fully formulated oils containing an alkyl disulfide antioxidant with the test compositions containing 1.0% to 2.5% of one of the additives generated in Examples 1–5 were tested for viscosity and spot dispersancy as in Example 6. Data is summarized in Table II and shows the composition containing the pyridyl phenyl ketimine functional group to be a superior antioxidant. This viscosity data was correlated with the relationship of polarographic half-wave potentials with the Paudler and Kress calculated energy of the nearest unoccupied molecular orbital for the corresponding nitrogen heterocyclic aromatic compounds. It was found that a linear relationship existed between the viscosity and energy data as previously known to exist between the energy and polarographic half-wave potentials. No composition containing an additive with energy less than or equal to that of the pyridyl phenyl ketimine had viscosity values higher than the control. Thus it can be concluded that their energies were too low to form the corresponding radical ion to function as a chain terminating species. The minimum energy required is that of the pyridine group. For a compound to be an antioxidation catalyst it must therefore have a calculated energy of the nearest unoccupied molecular orbital of 0.7 or more and a lubricant viscosity requiring 60 to 100 hours of use to increase by four hundred percent. This viscosity corresponds to a polarographic half-wave potential of about 1.3 to 2.3 volts.

TABLE II

| Additive Functional Group | Hours to Increase Initial Viscosity Four Times | Spot Dispersancy Test, % |
| --- | --- | --- |
| Control | 57 | 82 |
| Control | 56 | 80 |
| Pyridyl phenyl ketimine | 84 | 89 |
| Pyridyl 2,6-dialkyl 1-hydroxyl phenyl ketimine | 44 | — |
| Nicotinyl | 51 | 95 |
| 8-Carbonyl quinoline | 38 | 74 |
| Dipyridyl | 46 | — |

All control and test compositions were fully formulated oils containing an alkyl disulfide antioxidant.

We claim:

1. An antioxidant catalyst which functions as a chain terminating species in the chain oxidation reaction that occurs in lubricant compositions under conditions of use comprising an antioxidant additive having the structure $A[(X)_{m-1}Y]_n$ wherein:

(a) A is an antioxidant functional moiety selected from the group consisting of:

(1) nicotinyl having the structure:

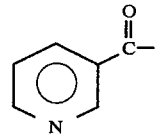

and (2) 8-carbonyl quinoline having the structure:

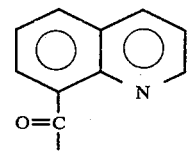

and (b) $[(X)_{m-1}Y]_n$ is an oil soluble moiety wherein:

(1) X is a divalent member connected directly to A and Y, respectively, and is selected from the group consisting of succinyl, imine, amino, and dialkyl piperazine succinimide having the structures:

 (i)

 (ii)

 (iii)

-continued

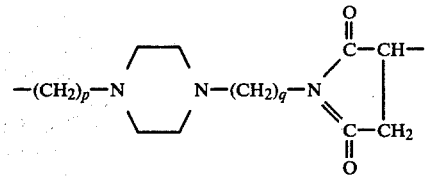
(iv)

wherein p and q are whole numbers from 1 to 6,
(2) m is a whole number from 1 to 2,
(3) Y is a monovalent aliphatic chain of from 12 to 50 carbon atoms whose valence is connected directly to X when m is 2 and directly to A when m is 1,
(4) n is a whole number from 1 to 2 and corresponds to the number of free valences in A; and
(c) when X is amino and m is 2; and when X is dialkyl piperazine succinimide and m is 2, A is any of the structures previously designated in (a) and n is from 1 to 2;
(d) when m is 1, A is any of the structures previously designated in (a) and n is from 1 to 2; whose calculating energy of the nearest unoccupied molecular orbital is greater than or equal to 0.7 and whose corresponding lubricant viscosity requires greater than or equal to 60 hours of use to increase to four times its initial value.

2. An antioxidant catalyst which functions as a chain terminating species in the chain oxidation reaction that occurs in lubricant compositions under conditions of use comprising an antioxidant additive having the structure $A[(X)_{m-1}Y]_n$ wherein:
(a) A is an antioxidant functional moiety selected from the group consisting of:
(1) nicotinyl having the structure:

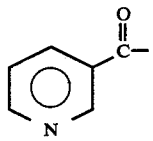

and
(2) 8-carbonyl quinoline having the structure:

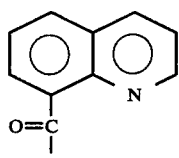

and
(b) $[(X)_{m-1}Y]_n$ is an oil soluble moiety wherein:
(1) X is a divalent member connected directly to A and Y, respectively, and is selected from the group consisting of succinyl, imine, amino, and dialkyl piperazine succinimide having the structures:

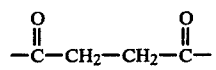
(i)

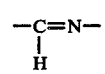
(ii)

-continued

H
|
—N—
(iii)

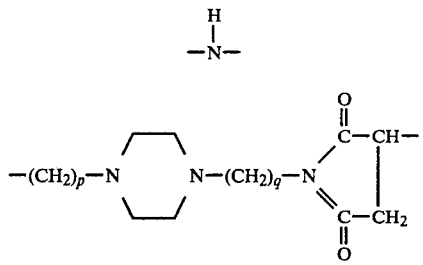
(iv)

wherein p and q are whole numbers from 1 to 6,
(2) m is a whole number from 1 to 2,
(3) Y is a monovalent aliphatic chain of from 12 to 50 carbon atoms whose valence is connected directly to X when m is 2 and directly to A when m is 1,
(4) n is a whole number from 1 to 2 and corresponds to the number of free valences in A; and
(c) when X is amino and m is 2, and when X is dialkyl piperazine succinimide and m is 2, A is any of the structures previously designated in (a) and n is from 1 to 2;
(d) when m is 1, A is any of the structures previously designated in (a) and n is from 1 to 2; whose polarographic half-wave potential is greater than or equal to 1.3 volts and whose corresponding lubricant viscosity requires greater than or equal to 60 hours of use to increase to four times its initial value.

3. A lubricating oil composition resistant to oxidative deterioration comprising a major proportion of hydrocarbon oil and about 0.1% to 10% of an additive having the structure $A[(X)_{m-1}Y]_n$ wherein:
(a) A is an antioxidant functional moiety selected from the group consisting of:
(1) nicotinyl having the structure:

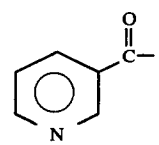

and
(2) 8-carbonyl quinoline having the structure:

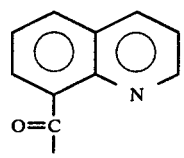

and
(b) $[(X)_{m-1}Y]_n$ is an oil soluble moiety wherein:
(1) X is a divalent member connected directly to A and Y, respectively, and is selected from the group consisting of succinyl, imine, amino, and dialkyl piperazine succinimide having the structures:

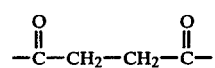
(i)

-continued

   (ii)

   (iii)

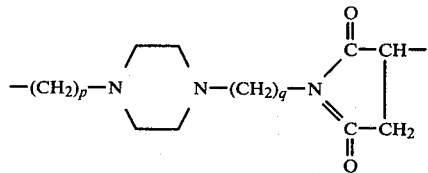   (iv)

wherein p and q are whole numbers from 1 to 6,
(2) m is a whole number from 1 to 2;

(3) Y is a monovalent aliphatic chain of from 12 to 50 carbon atoms whose valence is connected directly to X when m is 2 and directly to A when m is 1, (4) n is a whole number from 1 to 2 and corresponds to the number of free valances in A; and (c) when X is amino and m is 2, and when X is dialkyl piperazine succinimide and m is 2, A is any of the structures previously designated in (a) and n is from 1 to 2;

(d) when m is 1, A is any of the structures previously designated in (a) and n is from 1 to 2.

4. The composition of claim 3 containing said additive wherein A is nicotinyl, X is amino, Y is a $C_{12}$ to $C_{50}$ alkyl, m is 2, and n is 1.

5. The composition of claim 4 wherein the additive comprises nicotinyl octadecyl amide.

6. The composition of claim 3 containing said additive wherein A is 8-carbonyl quinoline, Y is a $C_{12}$ to $C_{50}$ alkyl, m is 1, and n is 1.

* * * * *

UNITED STATES PATENT OFFICE
CERTIFICATE OF CORRECTION

Patent No. 4,426,306  Dated January 17, 1984

Inventor(s) Richard J. Lee and Lynn M. R. Murphy

It is certified that error appears in the above-identified patent and that said Letters Patent are hereby corrected as shown below:

Patent reads:

| Col. | Line | | |
|------|------|---|---|
| 3 | 15-20 | partial formula reads | should read |

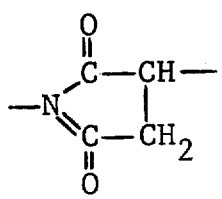 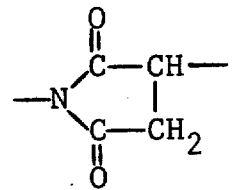

| Col. | Line | | |
|------|------|---|---|
| 4 | 54 | "60 of" should read --60 hours of-- | |
| 13 | 1-5 | partial formula reads | should read |

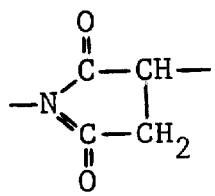 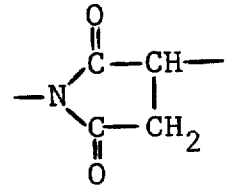

| | | | |
|---|---|---|---|
| 13 | 22-23 | "calculating" should read --calculated-- | |

UNITED STATES PATENT AND TRADEMARK OFFICE
CERTIFICATE OF CORRECTION

PATENT NO. : 4,426,306

DATED : January 17, 1984

INVENTOR(S) : Richard J. Lee and Lynn M. R. Murphy

It is certified that error appears in the above-identified patent and that said Letters Patent is hereby corrected as shown below:

Col. Line 14  5-11    partial formula reads        should read

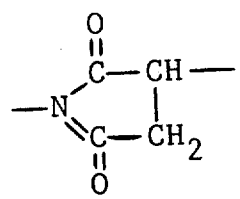
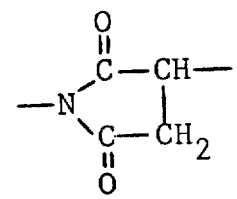

UNITED STATES PATENT AND TRADEMARK OFFICE
CERTIFICATE OF CORRECTION

PATENT NO. : 4,426,306          Page 3 of 3
DATED     : January 17, 1984
INVENTOR(S) : Richard J. Lee and Lynn M. R. Murphy It is certified that error appears in the above-identified patent and that said Letters Patent is hereby corrected as shown below:

Col.  Line 15    10-16 partial formula reads            should read

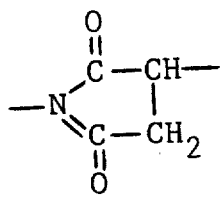   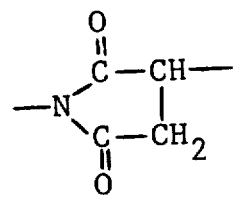

Signed and Sealed this

Twenty-second Day of May 1984

[SEAL]

Attest:

GERALD J. MOSSINGHOFF

Attesting Officer          Commissioner of Patents and Trademarks